(12) United States Patent
Duddu et al.

(10) Patent No.: US 8,153,786 B1
(45) Date of Patent: Apr. 10, 2012

(54) SYNTHESIS OF AZIDO HETEROCYCLES

(75) Inventors: Raja Duddu, Hackettstown, NJ (US); Paritosh Dave, Bridgewater, NJ (US); Reddy Damavarapu, Hackettstown, NJ (US); Rao Surapaneni, Long Valley, NJ (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 691 days.

(21) Appl. No.: 12/173,883

(22) Filed: Jul. 16, 2008

Related U.S. Application Data

(60) Provisional application No. 60/949,932, filed on Jul. 16, 2007.

(51) Int. Cl.
*C07D 257/00* (2006.01)
(52) U.S. Cl. ....................................................... 544/179
(58) Field of Classification Search .................. 544/179
See application file for complete search history.

(56) References Cited

OTHER PUBLICATIONS

Chavez et al., 1,2,4,5-Tetrazine Based Energetic Materials, Journal of Energetic Materials, vol. 17, No. 4, pp. 357-377, 1999.*

* cited by examiner

*Primary Examiner* — Brenda Coleman
(74) *Attorney, Agent, or Firm* — Henry S. Goldfine

(57) ABSTRACT

Energetic candidate azido heterocycles and their synthesis are described.

2 Claims, 6 Drawing Sheets

Scheme-1:

Reagents: i) ClCH$_2$COCl, heat  ii) NaN$_3$, Acetone. reflux

|  | 5 | 7 |
|---|---|---|
| Chemical Formula: | $C_{15}H_{18}N_{30}O_3$ | $C_{10}H_{12}N_{22}O_2$ |
| MW | 666.59 | 472.42 |
| Appearance: | Orange/red plate | Orange/red prism |
| Crystal size(mm): | 0.52x0.50x0.02 | 0.16x0.15x0.11 |
| Crystal System: | Monoclinic | Monoclinic |
| Temperature: | 294(2)K | -180C |
| Detector Distance (cm): | 5 | 5 |
| Frame Time: | 60/120 | 30 |
| Space Group: | C2/C | P21/n |
| Unit cell dimensions: | a:26.986(2)90 | a: 9.970 (5) 90 |
|  | b:14.3734(14)97.237(5) | b: 14.816(7) 104.320(9) |
|  | c: 15.4195(15) 90 | c: 13.602(7) 90 |
| Z: | 8 | 4 |
| Volume (Å3) | 5933.4(10) | 1946.8(16) |
| Density (Mg/m3): | 1.492 | 1.612 |
| (mm-1): | 1.006 | 0.127 |
| Goof: | 1.057 | 1.045 |
| $T_{min}$: | 0.593 | 0.980 |
| $T_{max}$: | 0.980 | 0.986 |
| Rint: | 0.0553 | 0.0488 |
| R1 (I>2): | 0.0703 | 0.0456 |
| wR2 (I>2): | 0.1988 | 0.1090 |
| R1 (all data): | 0.1125 | 0.0677 |
| wR2 (all data): | 0.2336 | 0.1186 |
| Reflections Collected: | 14441 | 15280 |
| Unique Reflections: | 5068 | 4698 |
| Max Resolution Å: | 0.83 | 0.75 |
| % Completeness: | 94.7 | 97.3 |

FIG. 6

SYNTHESIS OF AZIDO HETEROCYCLES

CROSS REFERENCE TO RELATED APPLICATION

This application claims the benefit of United States Provisional Application 60/949,932 filed July 16, 2007 the entire file wrapper contents of which are incorporated as if set forth at length herein.

FEDERAL INTEREST STATEMENT

The inventions described herein may be manufactured, used and licensed by the United States Government for United States Government purposes without payment of any royalties thereon or therefore.

FIELD OF THE INVENTION

This invention relates generally to the field of energetic compounds and in particular to a method for synthesizing azido heterocycles.

BACKGROUND OF THE INVENTION

The synthesis and development of new energetic ingredients have attracted the attention of synthetic organic chemists due to their utility in defense/military applications. Some of the recent examples in this context include polynitrocyclobutanes,[4] 1,3,3 ,-trinitroazeditine,[5] hexanitrohexaazaisowurtzitane (2,4,6,8,10,12-hexanitro-2,4,6,8,-10,12 hexaazatetracyclo [$5.5.0.0^{5,9}.0^{3,11}$]dodecane (CL-20)[6] and octanitrocubane. (See, e.g., Archibald, T. G.; Garver, L. C.; Baum, K.; Cohen, M. C.; Synthesis of polynitrocyclobutane derivatives. J. Org. Chem., 1989, 54 (12), 2869-2873; Archibald, T. G.; Gilardi, R.; Baum, K.; George, C.; Synthesis and X-ray crystal structure of 1,3,3-trinitroazetidine. J. Org. Chem., 1990, 55 (9), 2920-2924. b) Axenrod, T.; Watnick, C.; Yazdekhasti, H.; Dave, P. R.; Synthesis of 1, 3, 3-trinitroazetidine. Tetrahedron Lett., 1993, 34 (42), 6677-6680. c) Katritzky, A. R.; Cundy, D. J.; Chen, J.; Novel syntheses of 1,3,3-trinitroazetidine. J. Heteroccyclic Chem., 1994, 31 (2), 271-275. d) Axenrod, T.; Watnick, C.; Yazdekhasti, H.; Dave, P. R.; Synthesis of 1,3, 3-trinitroazetidine via the oxidative nitrolysis of N-p-tosyl-3-azetidinone oxime. J. Org. Chem., 1995, 60 (7), 1959-1964. e) Hiskey, M. A.; Coburn; M. D.; Synthesis of 1,3, 3-trinitroazetidine. U.S. Pat. No. 5,336,784, Aug. 09, 1994. f) Marchand, A. P. ; Rajagopal, D. ; Bott, S. G.; Archibald, T. G.; A novel approach to the synthesis of 1,3,3-trinitroazetidine. J. Org. Chem., 1995, 60 (15), 4943-4946. g) Hayashi, K.; Kumagai, T.; Nagao, Y.; Improved synthesis of an energetic material 1,3,3-trinitroazetidine exploiting 1-azabicyclo [1.1.0]butane. Heterocycles. 2000, 53 (2), 447-452.; Nielsen, A. T.; Chafin, A. P.; Christian, S. L.; Moore, D. W.; Nadler, M. P.; Nissan, R. A.; Vanderah, D. J.; Gilardi, R. D.; George, C. F.; Flippen-Anderson, J. L.; Synthesis of Polyazapoly-cyclic Caged Polynitramines. Tetrahedron, 1998, 54 (31), 11793-11812. b) Duddu, R.; Dave, P. R.; "Processes and compositions for nitration of N-substituted isowurtzitanes . . . " U.S. Pat. No. 6,015,898; Jan. 18, 2000. c) Duddu, R.; Dave, P. R.; "Processes and compositions for nitration of N-substituted isowurtzitanes . . . " U.S. Pat. No. 6, 160, 113; Dec. 12, 2000. d) Sysolyatin, S. V.; Lobanova, A. A.; Chernikova, Y. T.; Sakovich, G. V.; Methods of synthesis and properties of hexanitrohexaazaisowurtzitane. Russ. Chem. Rev., Russ. Chem. Rev., 2005, 74(8), 757-764; Zhang, M.; Eaton, P. E.; Gilardi, R.; Hepta- and octanitrocubanes. Angew. Chem. Int. Ed. . ., 2000, 39 (2), 401.

SUMMARY OF THE INVENTION

An advance is made in the art according to the principles of the present invention directed novel heterocyclic compounds containing mono- and poly-azido substitutions and their method of preparation.

More particularly, according to an aspect of the present invention, Azidoacetyl Pentanitrohexaazaisowurtzitane is prepared from Pentanitrohexaazaisowurtzitane, Cyanuric Chloride and Dichlorotetrazine whereby the Pentanitrohexaazaisowurtzitane is reacted with Chloroacetyl Chloide and the reaction products subsequently treated with Sodium Azide in Acetone under reflux conditions.

According to another aspect of the present invention, tris-triaxidomethylmethyloxy triazine and bis-triazidomethylmethyloxytetrazine are prepared by treating Cyanuric Chloride and Dichlorotetrazine with stoichiometric amounts of the sodium salt of triazidoalcohol in Tetrahydrofuran (THF) under reflux conditions.

In summary, successful preparation and isolation of azidoacetylpentanitro-hexaazaisowurtzitane (3), tris-(triazidomethyl)methoxytriazine (5), and bis(triazidomethyl)methoxytetrazine (7), along with X-ray structural characterization of 5 and 7 are reported.

BRIEF DESCRIPTION OF THE DRAWING

Further features and advantages of the present invention may be understood from the drawing in which:

FIG. 6 is a table showing X-ray structural data for tristriazdomethylmethyloxy triazine and bis-triazidomethylmethloxytetrazine.

DETAILED DESCRIPTION

The following merely illustrates the principles of the invention. It will thus be appreciated that those skilled in the art will be able to devise various arrangements which, although not explicitly described or shown herein, embody the principles of the invention and are included within its spirit and scope.

Furthermore, all examples and conditional language recited herein are principally intended expressly to be only for pedagogical purposes to aid the reader in understanding the principles of the invention and the concepts contributed by the inventor(s) to furthering the art, and are to be construed as being without limitation to such specifically recited examples and conditions.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

Figure 1:
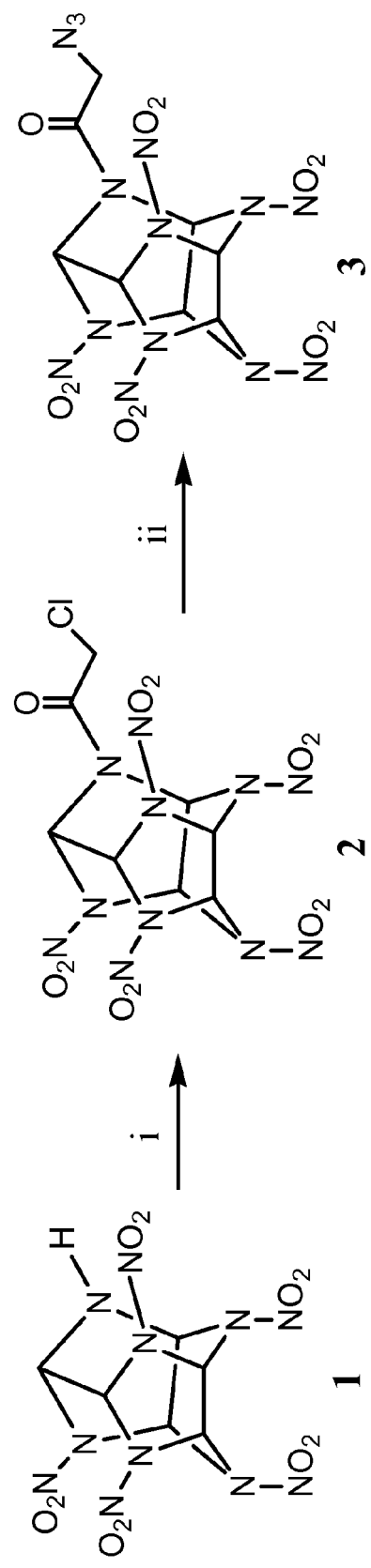
FIG. 1 is a reaction scheme for azidoacetyl pentanitrohexaazaisowurtzitane according to an aspect of the present invention.

Turning now to FIG. 1, there is shown a reaction scheme for the production of azidoacetyl pentanitrohexaazisowurzitane (3) according to an aspect of the present invention. In particular, pentanitrohexaazaisowurtzitane (1), (See, e.g., Bellamy, A. J.; 31$^{st}$ Intl Annual Conference of ICT, Karlsruhe, Germany, Jun. 27-30, 2000, 109-1 b) Lukyanov, O. A.; Shlykova, N. I.; Pentanitro- and Pentanitroso-2,4,6,8,10,12-hexaazoisowurtzitanes. Russ. Chem. Bull (English)., 2004, 53(3), 539-541 c) Duddu, R.; Dave, P. R.; Damavarapu, R.; Surapaneni, R.; Gilardi, R.; Hydrogenolytic denitration of polynitro compounds. Syn. Comm., 2005, 35(20), 2709-2714. d) Lukyanov, O. A.; Shlykova, N. I.; Penatnitro- and p entanitroso-2, 4,6,8,10,12-hexaazaisowurtzitanes . Russ. Chem. Bull. Int. Ed (Engl. Transl.)., 2004, 53 (3), 566-568.), is reacted with with chloroacetyl chloride to produce a corresponding chloro derivative (2) which upon treatment with sodium azide in acetone under reflux conditions affords azido compound ($^3$).

Figure 2:
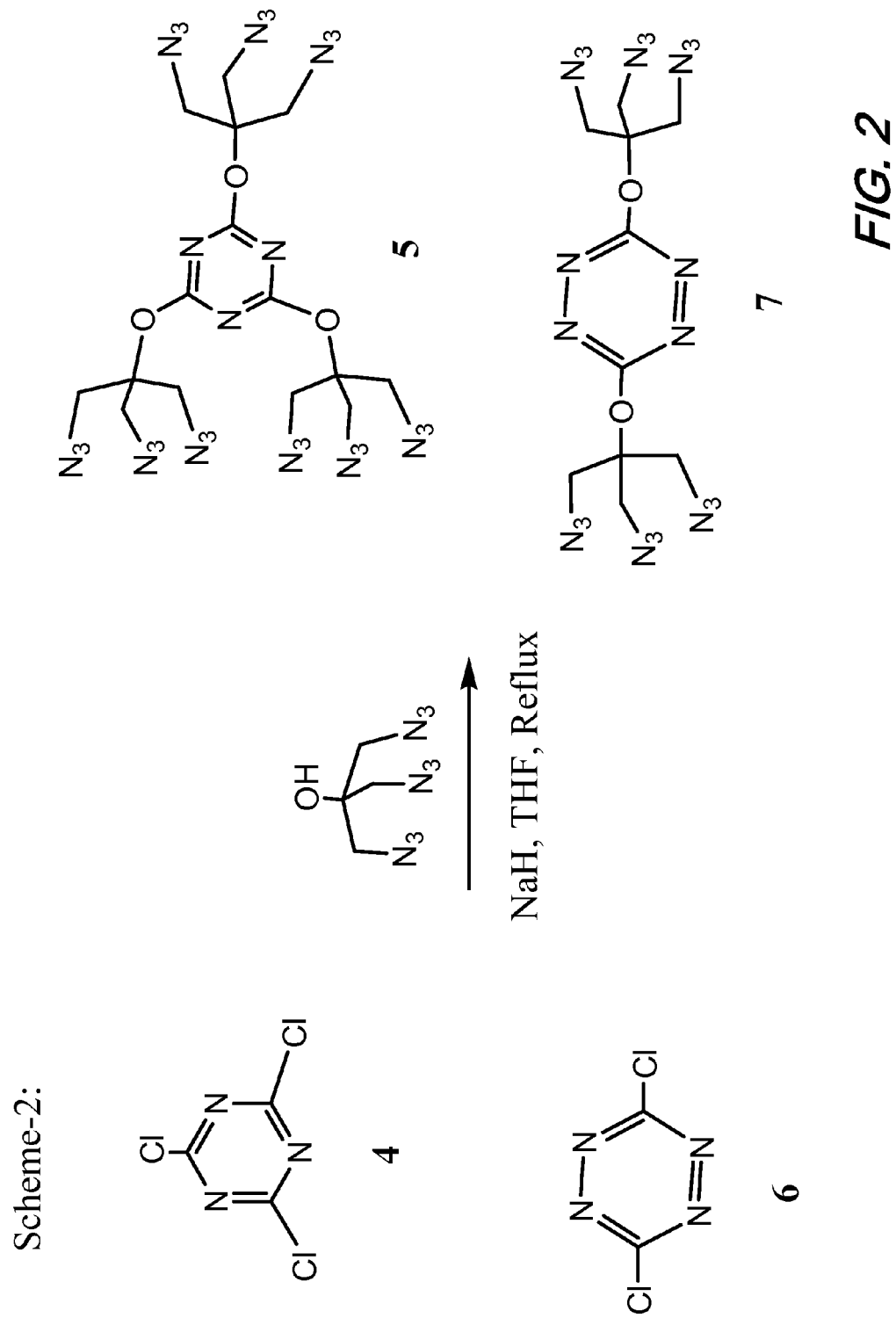
FIG. 2 is reaction scheme for tris-triazdomethylmethyloxy triazine (5) and bis-triazidomethylmethyloxytetrazine (7) according to another aspect of the present invention.

With reference now to FIG. 2, there is shown a reaction scheme for the production of tris-triazidomethylmethyloxy triazine (5) and bis-triazidomethylmethyloxytetrazine (7) according to another aspect of the present invention. More particularly, cyanauric chloride (4) and dichlorotetrazine (6) (See, e.g., Chavez, D. E.; Hiskey, M. A.; 1,2,4,5-Tetrazine based energetic materials. J. energetic. materials., 1999, 17, 357) are treated with stochiometric amounts of the sodium salt of triazidoalcohol (See, e.g., Dave, P. R.; Duddu, R.; Damavarapu, R.; Gelber, R.; Yang, K.; Surapaneni, C. R.; "Polyazido compounds". U.S. Pat. No. 6, 841,690 B1; Jan. 11, 2005. b) Dave, P. R.; Duddu, R. G.; Gelber, N.; Yang, K.; Surpaneni, C. R.; Preparation of cage molecule based polyazido core units for dendrimer synthesis. Tetrahedron Lett., 2004, 45(10), 2159) in THF under reflux conditions. The products (5) and (7)—after work up—were isolated as solids in 72 and 52% yields respectively. Their structures were established unambiguously with single crystal X-ray crystallography.

Experimental

All melting points were recorded by a capillary melting point apparatus and uncorrected. The IR spectra were determined on a Perkin-Elmer FT-IR Spectrum-2000 spectrometer. $^1$H and $^{13}$C NMR spectra were recorded on a Bruker Avance 400 MHz NMR spectrometer with CDCl$_3$ and acetone-d6 solvents. The chemical shift values were reported in 6 units (part per million) relative to TMS as an internal standard.

Azidoacetyl pentanitrohexaazaisowurtzitane (3): A mixture of pentanitro-hexaazaisowurtzitane (1.0 gm, 2.54 mmol) and chloroacetyl chloride (5 ml, excess) was heated in a sealed tube at 100° C. for 48 h. The reaction mixture was cooled to room temperature and evaporated to dryness. The residue was treated with ether, filtered, washed the solid with ether and air dried at room temperature to obtain 3 as a white solid. Yield: (0.98 gm, 82%). m.p: 201-202° C.; IR(KBr): 3040 (s), 1719 (s), 1593 (br, vs), 1325 (br, vs), 1275 (br, vs), 1155 (m), 1045 (m), 940 (s), 877 (s) Cm$^{-1}$; $^1$H NMR (Acetone-d6): 4.52 (s, 2H), 7.82 (br s, 1H), 7.98 (d AB, J$_{AB}$=8.0 Hz, 1H), 8.05 (d, J=8.0 Hz, 1H), 8.22 (d AB, J$_{AB}$=8.0 Hz, 1H), 8.28 (br s, 2H); Compound 5 was used as such without any further purification. Thus, the chloroacetyl substrate 5 (238 mg, 0.50 mmol) in acetone (5 mL) was treated with sodium azide (0.65 gm, 10 mmol) and the resulting heterogeneous mixture was refluxed for 12h. The reaction mixture was cooled to room temperature and filtered. The filtrate was evaporated and the residue was column chromatographed with si-gel (10% ethyl acetate: hexane as eluting solvent) to afford the product as a white solid. Yield: (214 mg, 88%). m.p: 109-111° C.; IR (KBr): 3040 (m), 2121 (s), 1709 (s), 1595 (vs), 1397 (m), 1267 (br, vs), 1165 (m), 1049 (s) cm$^{-1}$; $^1$H NMR (Acetone-d6): 4.34 (s, 2H), 7.81 (br s, 1H), 7.96 (d AB, J$_{AB}$=8.0 Hz, 1H), 8.02 (d, J=6.6 Hz, 1H), 8.20 (d AB, J$_{AB}$=8.0 Hz, 1H), 8.28 (br s, 2H); $^{13}$C NMR (Acetone-d6): 50.80, 68.59, 71.75 (2C), 71.82, 72.76, 76.04, 166.43.

Tris-triazidomethylmethyloxy triazine (5): A three neck 50 mL round bottom reaction flask equipped with a reflux condenser, magnetic stirring bar and a rubber septum was charged with a 95% NaH (84 mg, 95%, 3.3 mmol) and dry THF (10 mL) under nitrogen atmosphere. To this resulting suspension was added drop-wise triazidoalcohol (597 mg, 3.03 mmol) in dry THF (5 mL) via syringe. The mixture was stirred in a preheated (80° C.) oil bath for 3h. The reaction mixture was cooled to room temperature and was then added in portions cyanuric chloride (184mg, 1.0 mmol). After complete addition of cyanuric chloride, the reaction mixture was subjected to reflux for 7 days. Reaction mixture was cooled to room temperature and poured over crushed ice and extracted with ethylacetate (3x 25 mL). The combined organic layer was washed with water (1x 30 mL), brine (1x 30 mL) and dried (Na2SO4). Evaporation of the solvent followed by Si-gel column chromatography (5% EtOAc-Hexane) afforded the pure product as a white solid in 72% (480 mg) yield. m.p.: 74-75° C.; density: 1.473g/cc (measured by gas pycnometer); IR (KBr): 2933 (s), 2866 (m), 2551 (m), 2527 (m), 2103 (vs), 1731 (m), 1563 (vs), 1448 (vs), 1331 (vs), 1129 (vs) cm$^{-1}$; $^1$H-NMR (CDCl$_3$): 3.91 (s, 18H, 9x CH2); $^{13}$C-NMR (CDCl$_3$): 50.76, 85.58, and 170.90.

Bis-triazidomethylmethyloxytetrazine (7): Reaction was carried out following the reaction conditions as mentioned above using dichlorotetrazine (150 mg, 1.0 mmol), triazidoalchol (396 mg, 2.01 mmol) and sodium hydride (49 mg, 95%, 2.01 mmol) in THF (15 mL) under reflux for 4 days. The pure product was obtained as a fluorescent pink solid in 52% (245 mg) yield; m.p.: 111-112° C.; IR (KBr): 2927 (w), 2115 (vs), 1695 (br m), 1445 (vs), 1406 (vs), 1303 (s), 1096 (s) 1053 (s) cm$^{-1}$ $^1$H-NMR (CDCl$_3$): 3.97 (s, 12H, 6xCH2); $^{13}$C-NMR (CDCl$_3$): 50.91, 86.05, and 165.28.

Figure 3:
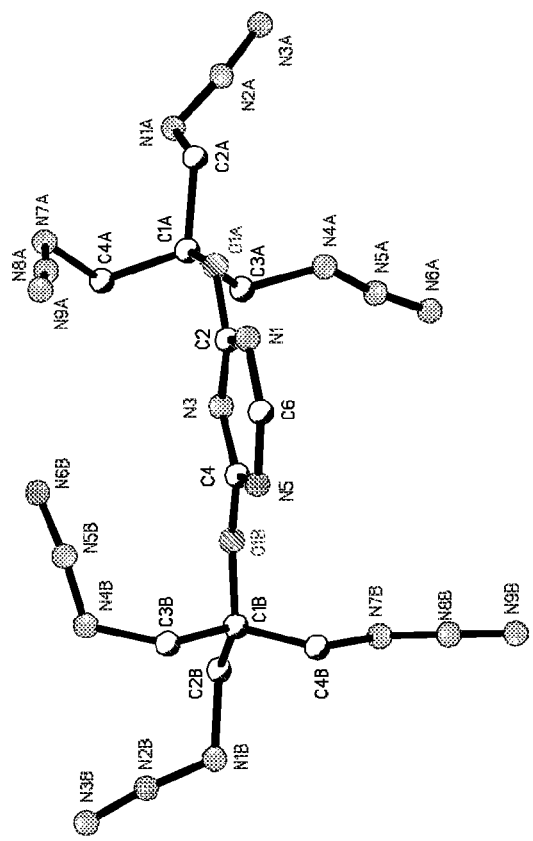
FIG. 3 is view of tris-triazdomethylmethyloxy triazine in which (3A) H atoms and the "B" substituent on the triazine ring are omitted and, (3B) the H atoms and the "C" substituent on the triazine ring are omitted.
Figure 3:
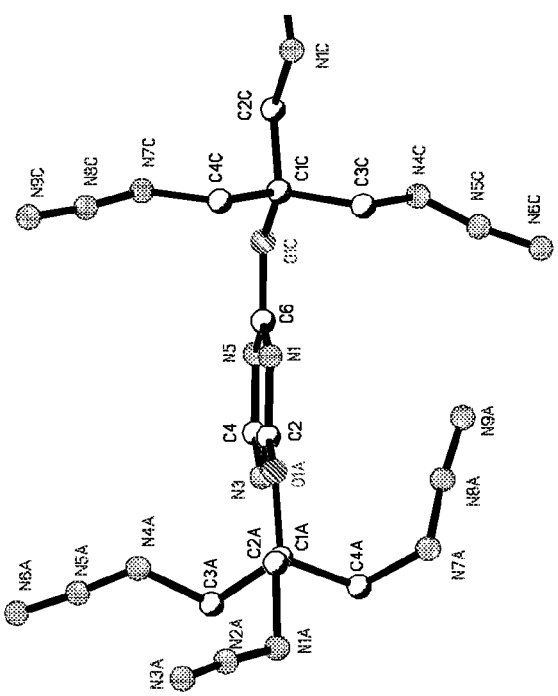

Turning now to FIG. 3 there is shown: FIG. 3(A) a view of the tris-triazidomethylmethyloxy triazine (5) omitting H atoms and the "B" substituent on the triazine ring and FIG. 3(B) a view of the tris-triazidomethylmethyloxy triazine (5) omitting H atoms and the "C" substituent on the triazine ring. The substituents are chemically identical, but display different combinations for the torsional conformations of the azido arms. One purpose of this simplification is to show the substituents without mutual overlap.

Figure 4:
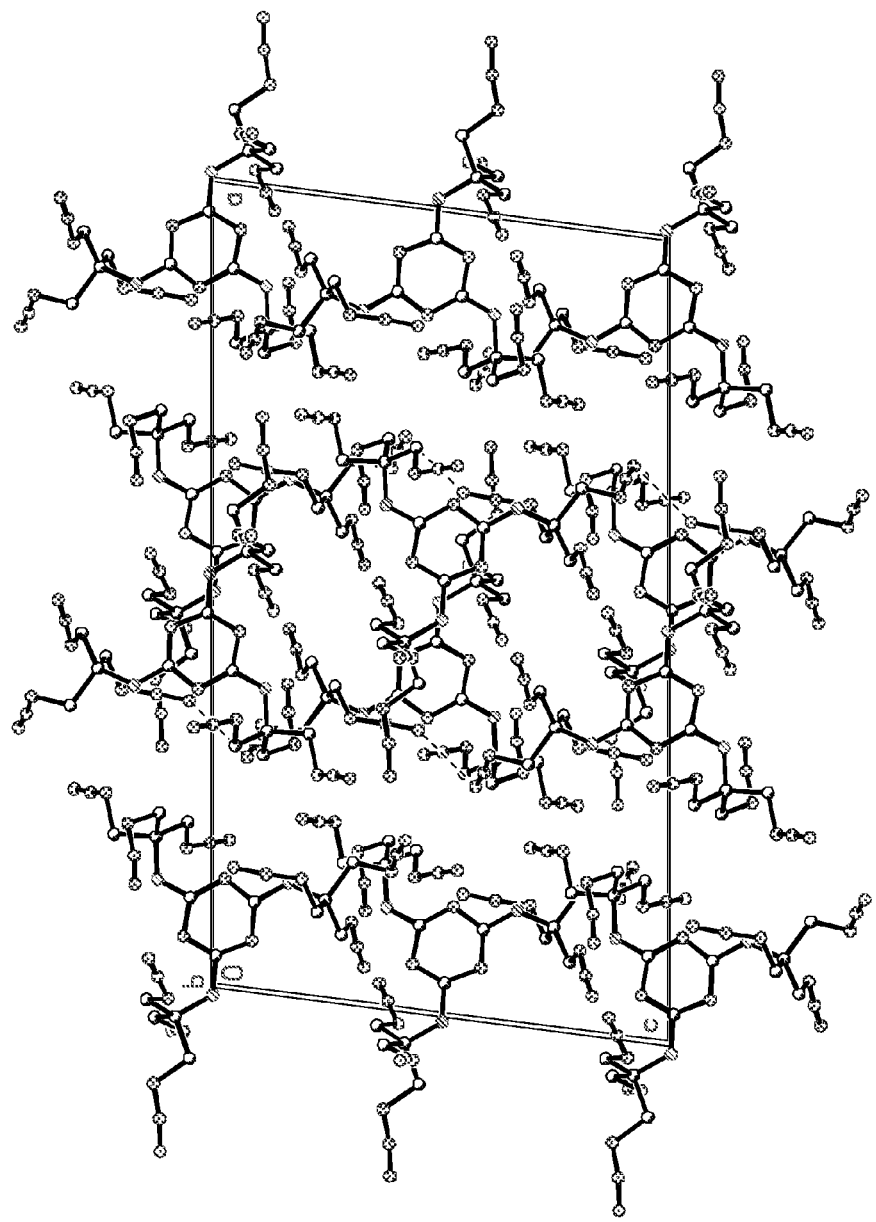
FIG. 4 is a view down the b axis of the unit cell of the packing in the crystal of tris-triazdomethylmethyloxy triazine.
Figure 5:
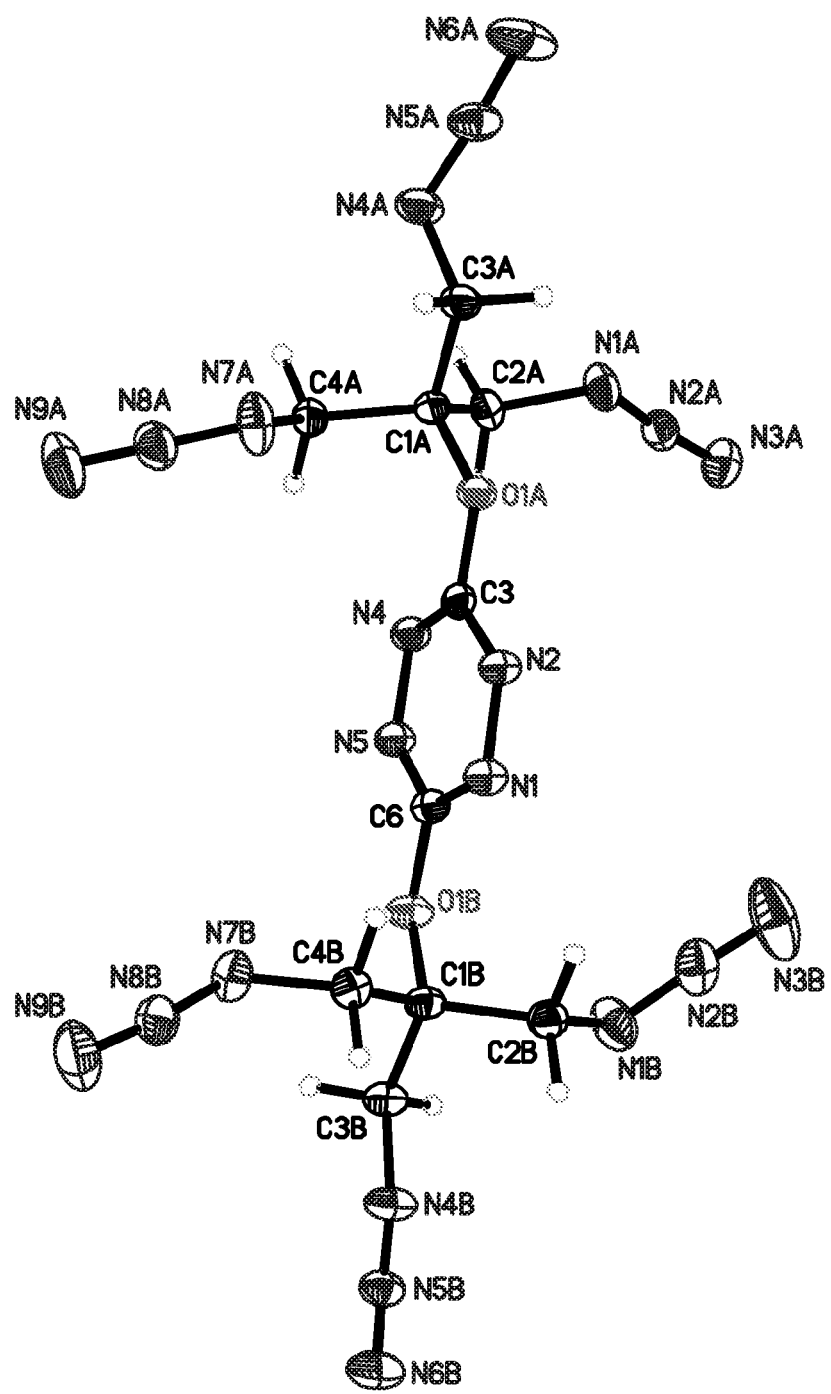
FIG. 5 is an ortep view of bis-triazidomethylmethloxytetrazine.

FIG. 4 shows a view down the b axis of the unit cell of the packing in the crystal of tristriazidomethylmethyloxy triazine (5). FIG. 5 shows an Ortep view of the bis-triazidomethylmethyloxytetrazine (6) and FIG. 6 is a table showing X-ray structural data for the tristriazidomethylmethyloxy triazine (5) and bis-triazidomethylmethyloxytetrazine (6).

At this point, while we have discussed and described the invention using some specific examples, those skilled in the art will recognize that our teachings are not so limited. For example, the preferred embodiments of the invention have been provided for the purpose of explaining the principles of the invention and its practical application, thereby enabling others skilled in the art to understand the invention. Various embodiments and various modifications are contemplated. Accordingly, the invention should be only limited by the scope of the claims attached hereto.

The invention claimed is:
1. The azido heterocycle bis-triazidomethylmethyloxytetrazine.

2. A method of preparing bis-triazidomethylmethvloxvtetrazine comprising the steps of:
treating cyanuric chloride and dichloroetrazine with stoichiometric amounts of the sodium salt of triazidoalcohol in THF under reflux conditions; and
the recovercdrecovering the azido heterocycle compound of bis-triazidomethylmethyloxytetrazine.

* * * * *